June 9, 1959 C. SKIMINA Plant Pat. 1,841
LANTANA PLANT
Filed July 14, 1958
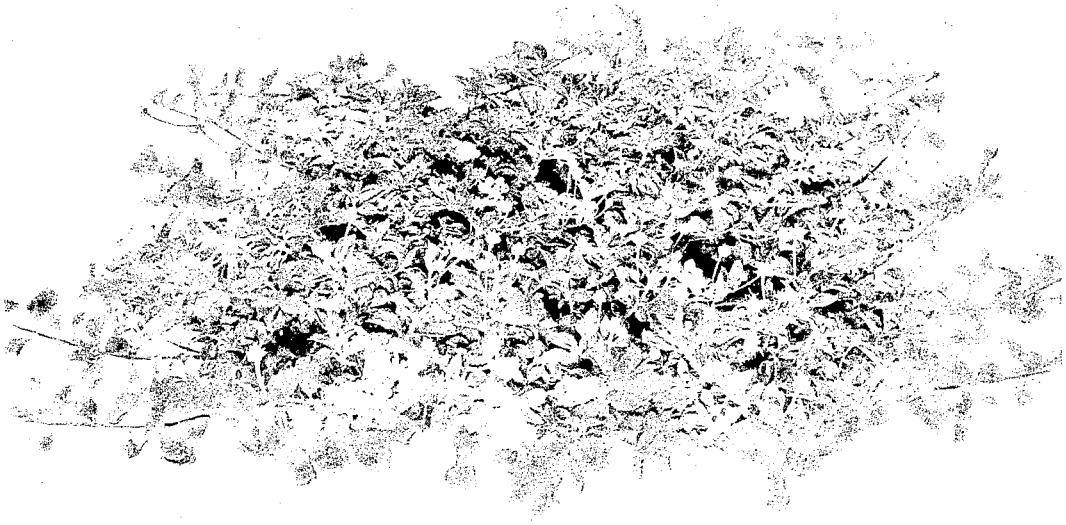
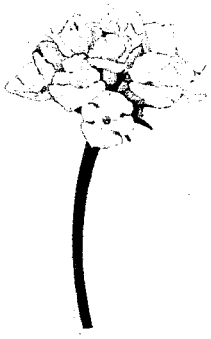
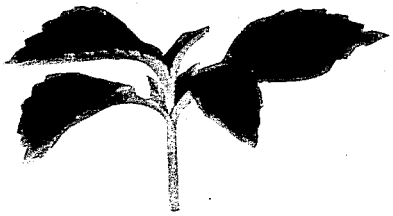
INVENTOR.
CONRAD SKIMINA
BY J. F. Cuneo
ATTORNEY United States Patent Office Plant Pat. 1,841
Patented June 9, 1959

1,841

LANTANA PLANT

Conrad Skimina, Azusa, Calif., assignor to Monrovia Nurseries Co., Azusa, Calif., a corporation of California Application July 14, 1958, Serial No. 748,550

1 Claim. (Cl. 47—60)

The present invention relates to a new and distinct variety belonging to the Lantana genus that is characterized as to novelty by its prostrate growing habit, abundance of large leaves and cream colored flowers. This plant has resulted from the cross breeding by me of *Lantana camara* Dwarf White, an unpatented upright variety, and *Lantana callowiana* Gold Rush, United States Plant Patent No. 1,211, after conducting numerous experiments in the Los Angeles area of southern California.

Cross breeding of the above identified species of Lantana has produced a new type as well as a new variety of Lantana that combines some of the characteristic features of each of its parent plants. The new variety distinguishes from it parent plant *Lantana camara* Dwarf White, in that its flowers are creamy yellow and its growth is prostrate instead of upright, and the plant forms a densely foliated shrub having vine-like stems. The novel variety of Lantana differs from its parent plant *Lantana callowiana* Gold Rush in that the flowers are a creamy yellow, the leaves are much larger and darker in color, and the plant is a more vigorous grower.

The blooms of the new variety are made up of groups of individual florets arranged in a substantially hemispherical umbel. The number of florets in each umbel appears to vary very slightly.

The accompanying illustrations include a black and white photograph showing the vine-like growth of the new variety of Lantana that clearly brings out its prostrate or trailing habit. The illustrations also include a full color reproduction of a single umbel and a full color representation of a typical leaf branch that shows the shape, size and color of the leaves.

The novel variety of Lantana has been reproduced asexually by me in the Los Angeles County area of southern California by means of cuttings. The distinguishing characteristics have been observed to be well established in all of the resulting plants. It has also been determined that the new species of Lantana cannot be reproduced by sexual means, the species will not reproduce true from seed.

A detailed description of the new and distinct variety of Lantana follows. All references to color names and numbers which are listed in the description are taken from the standards shown in the Horticultural Colour Chart adopted by the British Colour Council.

*The plant*

Nature and growth: The plant is best described as being of the trailing or prostrate type. The plant forms a densely foliated shrub that puts out many vine-like branches as is readily observed in the accompanying black and white photograph. These vine-like branches are approximately three feet long. The growth emanates from a central root structure.

Stems: The stems are slender and vine-like. The newly formed stems are at first succulent and attain as they become older a more woody structure. When the stems have reached maturity they become stiff and are quite brittle.

Leaves: The foliage of the plant is persistent and is moderately dense and possesses the following characteristics:

*Size.*—The leaves average seven eighths of an inch in width and are generally about one and three eighths inches in length.

*Shape.*—The leaves are broadly ovate, having serrated edges, the apex of the leaves is acuminate. The base of the leaf is rounded.

*Arrangement.*—The arrangement of the leaves is opposite; each leaf is attached to its respective stem by a short peduncle.

*Color.*—The predominant color of the leaves is Spinach Green 0960.

*Appearance and texture.*—The surface of the leaves is slightly pubescent. The leaves are slightly creased and have a leathery appearance. The ribs are quite prominent on the under side of the leaf.

*Aroma.*—The leaves have a strong aroma that can be described as similar to the aroma of oil of eucalyptus, but at the same time is reminiscent of the odor of sage.

Blooming habit: The plant is a profuse bloomer.

*The flower*

Arrangement: The individual flowers are clustered together and form a substantially hemispherical umbel that varies in size from about one to one and a quarter inches in diameter. Each of the umbels contains from about seventeen to nineteen florets. The umbels are formed on strong axillary stems or peduncles that average from two and a quarter to two and a half inches in length. The peduncles that support the flower umbel show no pubescence. The flowers are found exclusively in most instances on terminal growth.

Florets:

*Size.*—The individual florets are quite small ranging between five sixteenths and three eighths of an inch in width.

*Color.*—The color of the major portion of the individual florets is Sulfur Yellow No. 1/3, with the eye of the individual florets being Buttercup Yellow No. 5/1.

*Aroma.*—The aroma of the flowers is faint resembling that of the leaves.

Having described my invention, I claim:

The new and distinct variety of Lantana plant, substantially as herein shown and described, characterized especially by its abundance of faintly aromatic flowers and its combination of prostrate, trailing growth habit of *Lantana callowiana* Gold Rush, with the cream-pale yellow flower coloration and the larger and darker colored leaves of *Lantana camara* Dwarf White.

No references cited.